United States Patent [19] — [11] 4,221,792
Dolman et al. — [45] Sep. 9, 1980

[54] COMPOSITION ACTIVE AGAINST *PYRICULARIA ORYZAE*

[75] Inventors: Hendrik Dolman; Johannes Kuipers, both of Weesp, Netherlands

[73] Assignee: Duphar International Research, B.V., Weesp, Netherlands

[21] Appl. No.: 952,376

[22] Filed: Oct. 18, 1978

[30] Foreign Application Priority Data

Nov. 4, 1977 [NL] Netherlands .......................... 7712169

[51] Int. Cl.$^2$ .......................... A01N 9/00; A01N 9/22; C07D 265/00; C07D 273/00

[52] U.S. Cl. .................................... 424/249; 544/221; 544/223

[58] Field of Search ................. 424/249; 544/221, 223

[56] References Cited

U.S. PATENT DOCUMENTS

| | | | |
|---|---|---|---|
| 3,145,142 | 8/1964 | Lansbury | 424/249 |
| 3,396,167 | 8/1968 | Davies | 544/221 |
| 3,624,252 | 11/1971 | Labarge | 424/249 |
| 3,682,909 | 8/1972 | Hagemann | 544/221 |

OTHER PUBLICATIONS

Izv. Akad. Nauk SSSR, Ser. Khim., 1964 (11), 2051-2055.

*Primary Examiner*—Douglas W. Robinson
*Attorney, Agent, or Firm*—Norman N. Spain

[57] ABSTRACT

The compound of N,N',N"-trimethyl trithioisocyanurate and the novel compound N,N',N"-trimethyl 2-iminodithioisocyanurate have been found to be effective in protecting rice against *Pyricylaria oryzae.*

7 Claims, No Drawings

COMPOSITION ACTIVE AGAINST *PYRICULARIA ORYZAE*

BACKGROUND OF THE INVENTION

1. Field of the Invention

The instant invention relates to a composition which is active against *Pyricularia oryzae* on rice. The invention furthermore relates to the preparation of fungicidal compounds employed in said composition, as well as to a novel fungicidal isocyanurate.

2. Description of the Prior Art

In Izv. Akad. Nauk. SSSR, Ser. Khim, 1964 (11), 2051–2055 a compound is described of the formula

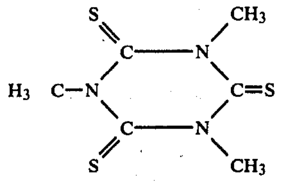

SUMMARY OF THE INVENTION

According to the invention it has now been found that compounds of the general formula

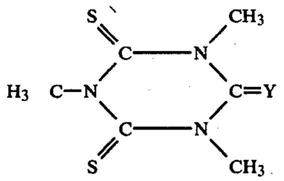

wherein Y is a sulphur atom or an imino group, have a strong fungicidal activity against *Pyricularia oryzae* on rice. The fungicidally active compounds according to the invention are the N,N', N''-trimethyl trithioisocyanurate of the above-cited article and the novel compound N,N',N''-trimethyl 2-iminodithioisocyanurate.

It has been found in field tests that a good protection of rice against infestation by *Pyricularia oryzae* is obtained with the use of the above-mentioned fungicidally active compounds in quantities of from 100 to 800 g per hectare. The results of field tests have demonstrated in addition a curative action of the compounds of the invention against the above-mentioned mould.

DESCRIPTION OF THE PREFERRED EMBODIMENTS

For practical applications the compounds of the invention are used in composition form. In such compositions the active compound is mixed with solid carrier material or dissolved or dispersed in liquid carrier material, possibly in combination with auxiliary substances, such as emulsifiers, wetting agents, dispersing agents and stabilizers.

Examples of compositions according to the invention are aqueous suspensions, oily solutions and oily dispersions, solutions in organic solvents, pastes, dusting powders, wettable powders, miscible oils, granules, invert emulsions, aerosol compositions and smoke.

Granular compositions may be prepared for example by dissolving the active compound in a solvent and impregnating the resultant solution on a carrier material, such as pumice and attaclay or mineral non-porous granules (sand and ground marlow), organic granules (for example, dried coffee grounds and cut tobacco stems) possibly in the present of a binder.

A granular composition may alternatively be manufactured by compressing the active compounds together with powdered minerals in the presence of lubricating agents and binders, and to disintegrate and sieve the compressed produce to the desired grain size.

Dusting powders may be obtained by intimately mixing the active substance with an inert solid carrier material, for example in a concentration of 1 to 50% by weight. As examples of suitable solid carrier materials there may be employed talcum, kaolin, pipe clay, diatomacious earth, dolomite, gypsum, chalk, bentonite, attapulgite, and colloidal $SiO_2$ or mixtures of these and similar substances. Organic carrier materials, for example ground walnut shells may also be used.

Wettable powders may be prepared by mixing 10 to 80 parts by weight of a solid inert carrier, for example the above-mentioned carrier materials, with 10 to 80 parts by weight of the active compounds, 1 to 5 parts by weight of a dispersing agent, for example, the lignine sulfonates or alkylnaphthalene sulfonates known for this purpose, and preferably also with 0.5 to 5 parts by weight of a wetting agent, for example fatty alcohol sulfates, alkylaryl sulfonates or fatty acid condensation products.

For the preparation of miscible oils, the active compounds may be dissolved or finely divided in a suitable solvent which preferably is water immiscible and an emulsifier is added to the resultant solution. Suitable solvents are, for example, xylene, toluene, petroleum distillates which are rich in aromates, for example, solvent naphtha, distilled tar oil and mixtures of these solvents. As emulsifiers there may be used, for example, alkylphenoxypolglycol ethers, polyoxyethylenesorbitan esters of fatty acids or polyoxyethylene sorbitol esters of fatty acids. The concentration of the active compounds in said miscible oils is not restricted to narrow limits and may vary, for example, between 2 and 50% by weight.

In addition to a miscible oil, there may be employed, as a liquid and highly concentrated primary composition, a solution of the active compounds in a readily water miscible liquid, for example, acetone, to which solution a dispersing agent and possibly a wetting agent are added. When diluted with water shortly prior to or during spraying, an aqueous dispersion of the active compound is obtained.

In addition the active compounds may be formulated into aqueous compositions suitable for application to rice crops by suspending the compounds in water in the presence of a suitable dispersing agent such as lignine-sulfonate and/or wetting agents such as naphthalene sulfonate, an alkyl sulfate, an alkylbenzene sulfonate, or an alkylarylpolyoxethylene.

Further aqueous compositions may be formulated by first dissolving the active compound in a water-immiscible solvent, such as xylene and then emulsifying the resultant solution in water in the presence of an emulsifier, for example, a ricinus oil modified with polyoxyethylene groups or an alkylarylpolyoxyethylene.

When it is desired to treat large areas of the crops with a comparatively small quantity of the composition by air spraying, invert emulsions and solutions in organic solvents may be employed.

Invert emulsions may be prepared by emulsifying water in an oily solution or an oily dispersion of the active compound shortly before or during spraying.

Solutions of the active compound in organic solvents such as isophorone, dimethylformamide and dodecylbenzene may be prepared and may be employed with the possible addition of such phytotoxic reducing agents as wool fat, wool fatty acid or wool fatty alcohols.

An aerosol composition according to the invention may be obtained in the usual manner by incorporating the active compounds, possibly in a solvent, in a volatile liquid to be used as a propellant gas, for example, a mixture of chlorine-fluorine derivates of methane and ethane.

Smoke generating candles or smoke generating powders, that is compositions which can develop a fungicidal smoke while burning, may be obtained by forming the active compounds into a combustible mixture which may comprise, for example, as a fuel a sugar or a wood, preferably in a ground form, a substance to maintain combustion, for example ammonium nitrate or potassium chlorate, and furthermore a substance to delay combustion, for example, kaolin, bentonite and/or colloidal silicic acid.

In addition to the above-mentioned ingredients, the agents according to the invention may also comprise other materials known for use in fungicidal compositions.

For example, a lubricating agent, for example calcium stearate or magnesium stearate, may be added to the wettable powder or a mixture to be granulated. "Adhesives", for example, polyvinyl-alcohol-cellulose derivatives or other colloidal materials, for example casein, may also be added so as to improve the adhesion of the pesticidal agent to the crop.

Known pesticidal compounds may also be incorporated in the compositions according to the invention. As a result of this the activity spectrum of the composition is widened and synergism may occur.

The following known insecticidal, fungicidal and acaricidal compounds may be combined with the active compounds of the invention.

Insecticides, for example:

1. chlorinated hydrocarbons, for example 2,2-bis(p-chlorophenyl)-1,1-trichloroethane and hexachloro-epoxy-octahydro-dimethanonaphthalene;
2. carbamates, for example N-methyl-1-naphtyl-carbamate;
3. dinitrophenols, for example 2-methyl-4,6-dinitrophenol and 2-(2-butyl)-4,6-dinitrophenyl 3,3-dimethylacrylate;
4. organic phosphorus compounds, for example, dimethyl-2-methoxy-carbonyl-1-methylvinyl-phosphate; O,O-diethyl-O-p-nitrophenylphosphorthioate; N-monomethylamide of O,O-dimethyl-dithiophosphor acetic acid;
5. benzoylurea derivatives, for example N-(2,6-difluoro-benzoyl)-N'-(4-chlorophenyl)urea.

Acaricides, for example:

1. diphenylsulphides, for example p-chlorobenzyl p-chlorophenyl sulphide and 2,4,4',5-tetrachlorodiphenyl-sulphide;
2. diphenylsulphonates, for example p-chlorophenyl benzene-sulphonate;
3. methyl carbinols, for example 4,4-dichloro-α-trichloro methyl benzhydrol;
4. quinoxaline compounds, for example methylquinoxaline dithio-carbonate.

Fungicides, for example:

1. Organic tin compounds, for example triphenyl tin hydroxide and triphenyl tin acetate;
2. alkelenebisthiocarbamates, for example zinc ethylenebis-dithiocarbamate and manganese ethylenebisdithio-carbamate,
3. and furthermore 2,4-dinitro-6-(2-octyl-phenyl-crotonate), 1-bis(dimethylamino)phosphoryl-3-phenyl-5-amino-1,2,4-triazole, 6-methyl-quinoxaline-2,3-dithiocarbonate 1,4-dithioanthraquinone-2,3-dicarbonitrile, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N'dimethyl sulphonyl-diamide and tetrachloroisophthalonitrile.

The dosage of the composition according to the invention desired for practical applications will depend among other things on the active compound chosen, the form of composition, the kind of rice crop which is to be protected against mould infection, the state of the rice crop and the weather conditions.

In general it holds that favorable results are obtained in a dosage whih corresponds to 100–800 g of the active substance per hectare.

The preparation of N,N'N"-trimethyl trithioisocyanurate may be carried out as described in the above mentioned article from Izv. Akad. Nauk. SSSR by trimerization of methyl isothiocyanate. According to this article the trimerization is carried out in the presence of triethylamine and an epoxide, for example, ethylene oxide or propylene oxide, in a closed tube at 90° C. In this manner the desired product is obtained after a reaction time of 4 hours in a yield of 70%.

However, when said reaction is carried out in circumstances which are more acceptable for practical purposes, namely at a pressure of 1 atmosphere and a temperature of approximately 20° C., it is found that a satisfactory conversion is obtained only after a reaction time of 24 hours.

According to another aspect of the invention it has now been found that said trimerization can be carried out much more rapidly, also more economically, in the presence of sodium hydride as a catalyst in a dipolar organic solvent. Dimethylsulphoxide is preferably used as a solvent. In these reaction conditions a satisfactory conversion into the desired N,N',N"-trimethyl trithioisocyanurate is obtained in less than half an hour.

N,N',N"-trimethyl 2-iminodithioisocyanurate is a new compound and can be prepared in a manner which is known for the synthesis of related compounds. For example, this last-mentioned compound can be prepared from N,N'N"-trimethyl trithioisocyanurate by reaction with ammonia.

The invention will now be described in greater detail with reference to the following examples.

EXAMPLE 1

Preparation of N,N', N"-trimethyl trithioisocyanurate 60 g of methylisothiocyanate, 80 ml of dimethyl-sulfoxide and 15 ml of triethylamine are heated to 70° C. 1 g of a 55% sodium hydride dispersion in mineral oil is added to the resultant mixture while stirring; the temperature of the reaction mixture increasing to 112° C. After heating to 120° C. another 0.4 g of sodium hydride dispersion is added and again 0.2 g after 5 minutes. The reaction mixture is stirred at 120° C. for 10 minutes and then cooled. 200 ml of methanol are then added, followed by 500 ml of water, after which the resultant precipitate is sucked off and washed with methanol. N,N'N''-trimethyl trithioisocyanaurate is obtained in a yield of 40.8 g; melting point 164°-165.5° C.

EXAMPLE 2

Preparation of N,N',N''-trimethyl 2-iminodithioisocyanurate 9 g of N,N'N''-trimethyl trithioisocyanurate is added portionwise to 250 ml of acetonitrile while the ammonia solution is stirred and is led through the solution. After the addition of all the N,N'N''-trimethyl trithioisocyanurate, the addition of ammonia is continued for another 15 minutes. The whole reaction is carried out at room temperature. After leaving the reaction mixture to stand for 3 hours, it is filtered and the filtrate is evaporated to dryness. The resulting crude N,N'N''-trimethyl 2-iminodithioisocyanurate is purified by dissolving it in methylene chloride and column chromatography, methylene chloride being used as a solvent and acetone as an eluent. Recrystallization from methanol yields 1.9 g of pure N,N'N''-trimethyl 2-iminodithioisocyanurate of melting point 150° C.

EXAMPLE 3

A dispersible powder was obtained by thoroughly mixing 25 parts by weight of the active compound, 5 parts by weight of lignin sulfonate, 2 parts by weight of naphthalene sulfonate and 68 parts by weight by kaolin.

Sprayable liquids were obtained by dispersing the resultant dispersible powder into water in different concentrations in the presence of 400 parts per million of alkylphenolpolyothyethylene.

The crop to be protected against *Pyricularia oryzae* was then treated with the above-mentioned sprayable liquids by spraying young rice plants, approximately 10 cm high, planted in plots of 1 $m^2$, with the above-described sprayable liquids. The plants thus treated are then infected with *Pyricularia oryzae* by spraying the plants with an aqueous suspension containing per ml 20,000-50,000 spores of *Pyricularia oryzae*. The incubation then takes place at a temperature varying between approximately 10° C. overnight and approximately 30° C. in the daytime and an air humidity also varying therewith of 60 to 100% for approximately 70 hours. These conditions are reached by placing the plants in a hothouse. These treatments are repeated after 8, 29 and 36 days. After 44 days the treatment with the fungicidal composition is carried out again; infection and incubation are then delayed, however, for 4 days, until 48 days after the first treatment. The condition of the crop is evaluated at different instants between and after the various treatments.

The results of these evaluations are recorded in the following table. In the table the concentration of the compounds used is shown in ppm and the extent of infestation of the plants by *Pyricularia oryzae* which was found at the instant of evaluation is indicated by 0%-100%. 0% indicates no infection at the concentration employed, while 100% indicates total infection so that the plant has died.

Further in the table (1) = N,N',N''-trimethyl trithioisocyanurate
(2) = N,N',N''-trimethyl 2-iminodithioisocyanurate

| | | days after first treatment with fungicidal composition | | | | | | |
|---|---|---|---|---|---|---|---|---|
| | | 34 | 41 | 45 | 52 | 57 | 62 | 69 |
| compound | conc. in ppm | infestation in % at instant of evaluation (days after treatment) | | | | | | |
| (1) | 200 | 13 | 13 | 8 | 5 | 5 | 10 | 25 |
| | 400 | 5 | 5 | 5 | 0 | 0 | 5 | 10 |
| | 800 | 5 | 5 | 3 | 0 | 0 | 3 | 8 |
| (2) | 200 | 5 | 8 | 10 | 5 | 8 | 10 | 20 |
| | 400 | 5 | 5 | 5 | 3 | 3 | 5 | 10 |
| | 800 | 5 | 5 | 3 | 0 | 0 | 5 | 8 |
| control | — | 14 | 21 | 39 | 53 | 63 | 70 | 78 |

From the above table the strong activity of the compounds according to the invention against *Pyricularia oryzae* is clearly evident. Even in spite of a severe test, in which infection and incubation were carried out only 4 days after the treatment with the composition, the rice plants remained well protected against infestation by the mould. In particular when the active compounds were used in concentrations of at least 400 ppm the activity of the preparation did not decrease noticeably in these 4 days.

From the results shown, a curative action of the compounds against *Pyricularia oryzae* is also evident.

We claim:

1. A composition active against *Pyricularia oryzae* on rice, said composition comprising a fungicidally effective amount of a compound of the general formula

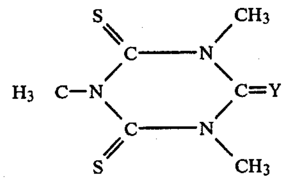

wherein Y is sulphur or imino and a liquid or finely divided solid carrier.

2. A composition of claim 1, wherein the active compound is N,N',N''-trimethyl trithioisocyanurate.

3. A composition active against *Pyricularia oryzae* on rice, said composition comprising a fungicidally effective amount of N,N',N''-trimethyl 2-iminodithioisocyanurate and a liquid or finely divided solid carrier.

4. A method of protecting a rice crop from infestation of *Pyricularia oryzae* comprising applying to said crop a composition of claim 2.

5. A method of protecting a rice crop from infestation of *Pyricularia oryzae* comprising applying to said crop a composition of claim 3.

6. A method of protecting a rice crop against infestation of *Pyricularia oryzae* comprising applying to said crop a composition of claim 2 in a dosage of 100 to 800 g of the active compound per hectare.

7. A method of protecting a rice crop against infestation of *Pyricularia oryzae* comprising applying to said crop a composition of claim 3 in a dosage of 100 to 800 g of the active compound per hectare.

* * * * *